United States Patent [19]

Bennett et al.

[11] Patent Number: 5,750,872
[45] Date of Patent: May 12, 1998

[54] NUCLEIC ACIDS ENCODING ASCORBATE FREE RADIAL REDUCTASE AND THEIR USES

[75] Inventors: Alan B. Bennett; David A. Brummell; Alexander A. Grantz, all of Davis, Calif.

[73] Assignee: The Regents of the University of California, Oakland, Calif.

[21] Appl. No.: 417,492

[22] Filed: Apr. 5, 1995

[51] Int. Cl.$^6$ .............................. A01H 5/00; C12N 15/29; C12N 15/84; C12N 15/82; C12N 15/53
[52] U.S. Cl. .................... 800/205; 800/DIG. 44; 435/172.3; 435/189; 536/23.6; 536/24.1
[58] Field of Search ................... 536/23.6, 24.1; 800/205, DIG. 44; 435/172.3, 189

[56] References Cited

PUBLICATIONS

Sano, Satoshi, et al. (1994) "cDNA Cloning of Monodehydroascorbate Radical Reductase from Cucumber: a High Degree of Homology in Terms of Amino Acid Sequence between This Enzyme and Bacterial Flavoenzymes", *Plant Cell Physiol.*, 35(3): 425–437.

Trümper, Susanne, et al. (1994) "A novel dehydroascorbate reductase from spinach chloroplasts homologous to plant trypsin inhibitor", *FEBS Letters* 352:159–162.

Murthy, Siva S., et al. (1994) "Molecular Cloning and Characterization of cDNA Encoding Pea Monodehydroascorbate Reductase", *The Journal of Biological Chemistry*, 269(49):31129–31133.

Hossain, M. Anwar, et al. (1985) "Monodehydroascorbate Reductase from Cucumber Is a Flavin Adenine Dinucleotide Enzyme", *The Journal of Biological Chemistry*, 260(24): 12920–12926.

Wells, William W., et al. (1993) "Thioltransferases", *Adv. in Enzym. Related Areas Mol. Biol.*, 66:149–201.

Napoli et al. 1990. Plant Cell 2: 279–289.

Smith et al. 1988. Nature 334: 724–726.

De Tullio et al. 1992. Boll. Soc. It. Biol. Sper. 68(10): 613–617.

*Primary Examiner*—David T. Fox
*Attorney, Agent, or Firm*—Townsend and Townsend and Crew LLP

[57] ABSTRACT

The present invention provides isolated nucleic acid constructs comprising tomato AFR reductase polynucleotide sequences. The polynucleotides encode AFR reductase polypeptides having ability to catalyze the reduction of AFR, which provide enhanced resistance to oxidative stress. The invention further provides transgenic plants comprising the recombinant expression cassettes, as well as methods of enhancing resistance to oxidative stress in a plant.

21 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1723 base pairs
        ( B ) TYPE: nucleic acid
        ( C ) STRANDEDNESS: single ( D ) TOPOLOGY: linear ( i i i ) HYPOTHETICAL: NO ( i x ) FEATURE:
    ( A ) NAME/KEY: exon
    ( B ) LOCATION: 49..643
    ( D ) OTHER INFORMATION: /number=1

( i x ) FEATURE:
    ( A ) NAME/KEY: intron
    ( B ) LOCATION: 644..780
    ( D ) OTHER INFORMATION: /number=1

( i x ) FEATURE:
    ( A ) NAME/KEY: exon
    ( B ) LOCATION: 781..1484
    ( D ) OTHER INFORMATION: /number=2

( i x ) FEATURE:
    ( A ) NAME/KEY: CDS
    ( B ) LOCATION: join(49..643, 781..1487)

( x i ) SEQUENCE DESCRIPTION: SEQ ID NO:1:

```
AATCTTCACC AAAAAAGCTC TAACTATTTT CACTGTGAAA GTTCATCA ATG GCG GAG        57
                                                      Met Ala Glu
                                                        1

AAA TCA TTC AAG TAT GTG ATC GTC GGT GGC GGT GTT TCT GCT GGG TAT       105
Lys Ser Phe Lys Tyr Val Ile Val Gly Gly Gly Val Ser Ala Gly Tyr
      5              10                  15

GCT GCT AGA GAA TTT GCC AAA CAG GGA GTT AAG CCT GGG GAA CTG GCT       153
Ala Ala Arg Glu Phe Ala Lys Gln Gly Val Lys Pro Gly Glu Leu Ala
 20              25                  30                  35

ATT ATT TCC AAA GAG GCA GTG GCT CCT TAT GAA CGT CCT GCA CTT AGC       201
Ile Ile Ser Lys Glu Ala Val Ala Pro Tyr Glu Arg Pro Ala Leu Ser
             40                  45                  50

AAG GCA TAC CTT TTT CCT GAA GGA GCT GCT AGA CTC CCA GGA TTT CAT       249
Lys Ala Tyr Leu Phe Pro Glu Gly Ala Ala Arg Leu Pro Gly Phe His
                 55                  60                  65

GTG TGT GTT GGA AGT GGA GGA GAG AGA CAG CTT CCT GAG TGG TAT GCA       297
Val Cys Val Gly Ser Gly Gly Glu Arg Gln Leu Pro Glu Trp Tyr Ala
             70                  75                  80

GAG AAA GGC ATT TCG TTG ATC CTG AGT ACT GAA ATA GTG AAA GCA GAT       345
Glu Lys Gly Ile Ser Leu Ile Leu Ser Thr Glu Ile Val Lys Ala Asp
         85                  90                  95

CTT GCT TCA AAG ACT CTT GTT AGT GCA GCT GGG GAA TCT TTT AAA TAT       393
Leu Ala Ser Lys Thr Leu Val Ser Ala Ala Gly Glu Ser Phe Lys Tyr
100             105                 110                 115

CAA ACA CTT GTT ATT GCA ACA GGT ACC ACC GTT TTG AAG TTG TCA GAT       441
Gln Thr Leu Val Ile Ala Thr Gly Thr Thr Val Leu Lys Leu Ser Asp
             120                 125                 130

TTT GGT GTA CAA GGT GCT GAT TCC AAG AAT ATC TTT TAC TTG AGA GAA       489
Phe Gly Val Gln Gly Ala Asp Ser Lys Asn Ile Phe Tyr Leu Arg Glu
             135                 140                 145

ATC GAT GAT GCT GAT CAA CTT GTG GAA GCA TTA AAA GCT AAG AAA AAT       537
Ile Asp Asp Ala Asp Gln Leu Val Glu Ala Leu Lys Ala Lys Lys Asn
         150                 155                 160

GGT AAA GCT GTT GTT GTT GGG GGA GGG TAC ATC GGT CTC GAG CTT AGT       585
Gly Lys Ala Val Val Val Gly Gly Gly Tyr Ile Gly Leu Glu Leu Ser
     165                 170                 175

GCT GTA CTG AGA CTG AAC AAC ATT GAA GTC AAT ATG GTT TAC CCA GAA       633
Ala Val Leu Arg Leu Asn Asn Ile Glu Val Asn Met Val Tyr Pro Glu
180                 185                 190                 195

CCA TGG TGC A GTAAGTAAAT TGCGTTTAGT TTGCACACTG CATGCATAAC             683
Pro Trp Cys
```

```
ATGAAATGTT ACACTGTTTC ATGGTAGTCT GTTATGGAGA ATATATTGTC CTGCTTAATT          743

GTATTGTTAT CTTACTGTAA TCCTTATGAT TTTCCAG  TG CCT CGG CTT TTC ACA          797
                                         Met Pro Arg Leu Phe Thr
                                             200

GAG GGC ATA GCT GCG TTC TAT GAA GGT TAT TAT AAA AAC AAG GGA GTC           845
Glu Gly Ile Ala Ala Phe Tyr Glu Gly Tyr Tyr Lys Asn Lys Gly Val
205                     210                 215                 220

AAT ATT ATC AAG GGT ACA GTG GCT GTT GGG TTT GAT ACC CAT CCA AAT           893
Asn Ile Ile Lys Gly Thr Val Ala Val Gly Phe Asp Thr His Pro Asn
                225                 230                 235

GGA GAG GTG AAG GAA GTC AAA CTC AAA GAT GGC AGA GTT TTG GAA GCT           941
Gly Glu Val Lys Glu Val Lys Leu Lys Asp Gly Arg Val Leu Glu Ala
            240                 245                 250

GAC ATA GTA GTC GTA GGA GTC GGA GCA AGA CCA CTC ACA ACT CTA TTC           989
Asp Ile Val Val Val Gly Val Gly Ala Arg Pro Leu Thr Thr Leu Phe
        255                 260                 265

AAA GGG CAA GTT GAA GAG GAG AAG GGT GGA ATT AAG ACA GAT GCG TTC          1037
Lys Gly Gln Val Glu Glu Glu Lys Gly Gly Ile Lys Thr Asp Ala Phe
    270                 275                 280

TTC AAA ACA AGT GTA CCT GAT GTA TAT GCT GTG GGT GAT GTT GCC ACT          1085
Phe Lys Thr Ser Val Pro Asp Val Tyr Ala Val Gly Asp Val Ala Thr
285                 290                 295                 300

TTT CCT TTG AAA ATG TAC AAT GAG ATT AGA AGA GTT GAA CAT GTT GAT          1133
Phe Pro Leu Lys Met Tyr Asn Glu Ile Arg Arg Val Glu His Val Asp
                305                 310                 315

CAT TCT CGC AAA TCT GCT GAG CAG GCT GTC AAG GCA ATA TTT GCC AGT          1181
His Ser Arg Lys Ser Ala Glu Gln Ala Val Lys Ala Ile Phe Ala Ser
            320                 325                 330

GAG CAA GGG AAG TCT GTC GAT GAA TAT GAC TAC CTT CCA TAC TTC TAT          1229
Glu Gln Gly Lys Ser Val Asp Glu Tyr Asp Tyr Leu Pro Tyr Phe Tyr
        335                 340                 345

TCC CGC GCC TTC GAT TTG TCT TGG CAA TTC TAC GGT GAT AAT GTG GGT          1277
Ser Arg Ala Phe Asp Leu Ser Trp Gln Phe Tyr Gly Asp Asn Val Gly
    350                 355                 360

GAA ACA GTG CTC TTT GGG GAC GCT GAT CCC AAC TCT GCA ACT CAC AAG          1325
Glu Thr Val Leu Phe Gly Asp Ala Asp Pro Asn Ser Ala Thr His Lys
365                 370                 375                 380

TTT GGA CAA TAC TGG ATC AAA GAT GGA AAG ATC GTT GGT GCA TTC CTC          1373
Phe Gly Gln Tyr Trp Ile Lys Asp Gly Lys Ile Val Gly Ala Phe Leu
                385                 390                 395

GAG AGT GGG TCA CCT GAA GAG AAC AAG GCA ATT GCT AAG GTT GCA AAG          1421
Glu Ser Gly Ser Pro Glu Glu Asn Lys Ala Ile Ala Lys Val Ala Lys
            400                 405                 410

GTT CAA CCC CCT GCT ACC TTG GAT CAA TTG GCA CAG GAG GGC ATC AGT          1469
Val Gln Pro Pro Ala Thr Leu Asp Gln Leu Ala Gln Glu Gly Ile Ser
        415                 420                 425

TTT GCC TCA AAG ATC TAA TTTTTATACC TACTTTGGAT TTTAAAACAG                 1517
Phe Ala Ser Lys Ile *
430

CTCTTTGAAG TTTCTGCCTT ATTTACAATG TTGTAATTGT TTGACATTTT TCATGGCTGT        1577

TTGATTGGTT TAAATATGAT GTTCTTCAT CTGAGTTTAG TTGCAGAAGA TCACCCTGTA         1637

AGGCATATAT ATTCATACCT TAAAGTGTGA CATCTCTGTA AATAATGAAT GTTAGAAGCA        1697

ATGTGGTTTG TGAAAAAAAA AAAAAA                                             1723
```

( 2 ) INFORMATION FOR SEQ ID NO:2:

( i ) SEQUENCE CHARACTERISTICS:
        ( A ) LENGTH: 433 amino acids
        ( B ) TYPE: amino acid ( D ) TOPOLOGY: linear ( i i ) MOLECULE TYPE: protein ( x i ) SEQUENCE DESCRIPTION: SEQ ID NO:2:

| Met | Ala | Glu | Lys | Ser | Phe | Lys | Tyr | Val | Ile | Val | Gly | Gly | Gly | Val | Ser |
| 1 | | | | 5 | | | | | 10 | | | | | 15 | |

| Ala | Gly | Tyr | Ala | Ala | Arg | Glu | Phe | Ala | Lys | Gln | Gly | Val | Lys | Pro | Gly |
| | | | 20 | | | | 25 | | | | | 30 | | | |

| Glu | Leu | Ala | Ile | Ile | Ser | Lys | Glu | Ala | Val | Ala | Pro | Tyr | Glu | Arg | Pro |
| | | 35 | | | | 40 | | | | | 45 | | | | |

| Ala | Leu | Ser | Lys | Ala | Tyr | Leu | Phe | Pro | Glu | Gly | Ala | Ala | Arg | Leu | Pro |
| | 50 | | | | | 55 | | | | | 60 | | | | |

| Gly | Phe | His | Val | Cys | Val | Gly | Ser | Gly | Gly | Glu | Arg | Gln | Leu | Pro | Glu |
| 65 | | | | | 70 | | | | | 75 | | | | | 80 |

| Trp | Tyr | Ala | Glu | Lys | Gly | Ile | Ser | Leu | Ile | Leu | Ser | Thr | Glu | Ile | Val |
| | | | | 85 | | | | | 90 | | | | | 95 | |

| Lys | Ala | Asp | Leu | Ala | Ser | Lys | Thr | Leu | Val | Ser | Ala | Ala | Gly | Glu | Ser |
| | | | 100 | | | | 105 | | | | | 110 | | | |

| Phe | Lys | Tyr | Gln | Thr | Leu | Val | Ile | Ala | Thr | Gly | Thr | Thr | Val | Leu | Lys |
| | | 115 | | | | 120 | | | | | 125 | | | | |

| Leu | Ser | Asp | Phe | Gly | Val | Gln | Gly | Ala | Asp | Ser | Lys | Asn | Ile | Phe | Tyr |
| | 130 | | | | | 135 | | | | | 140 | | | | |

| Leu | Arg | Glu | Ile | Asp | Asp | Ala | Asp | Gln | Leu | Val | Glu | Ala | Leu | Lys | Ala |
| 145 | | | | | 150 | | | | | 155 | | | | | 160 |

| Lys | Lys | Asn | Gly | Lys | Ala | Val | Val | Val | Gly | Gly | Gly | Tyr | Ile | Gly | Leu |
| | | | | 165 | | | | | 170 | | | | | 175 | |

| Glu | Leu | Ser | Ala | Val | Leu | Arg | Leu | Asn | Asn | Ile | Glu | Val | Asn | Met | Val |
| | | | 180 | | | | | 185 | | | | | 190 | | |

| Tyr | Pro | Glu | Pro | Trp | Cys | Met | Pro | Arg | Leu | Phe | Thr | Glu | Gly | Ile | Ala |
| | | | 195 | | | | 200 | | | | | 205 | | | |

| Ala | Phe | Tyr | Glu | Gly | Tyr | Tyr | Lys | Asn | Lys | Gly | Val | Asn | Ile | Ile | Lys |
| | | 210 | | | | | 215 | | | | | 220 | | | |

| Gly | Thr | Val | Ala | Val | Gly | Phe | Asp | Thr | His | Pro | Asn | Gly | Glu | Val | Lys |
| 225 | | | | | 230 | | | | | 235 | | | | | 240 |

| Glu | Val | Lys | Leu | Lys | Asp | Gly | Arg | Val | Leu | Glu | Ala | Asp | Ile | Val | Val |
| | | | | 245 | | | | | 250 | | | | | 255 | |

| Val | Gly | Val | Gly | Ala | Arg | Pro | Leu | Thr | Thr | Leu | Phe | Lys | Gly | Gln | Val |
| | | | 260 | | | | | 265 | | | | | 270 | | |

| Glu | Glu | Glu | Lys | Gly | Gly | Ile | Lys | Thr | Asp | Ala | Phe | Phe | Lys | Thr | Ser |
| | | | 275 | | | | 280 | | | | | 285 | | | |

| Val | Pro | Asp | Val | Tyr | Ala | Val | Gly | Asp | Val | Ala | Thr | Phe | Pro | Leu | Lys |
| | 290 | | | | | 295 | | | | | 300 | | | | |

| Met | Tyr | Asn | Glu | Ile | Arg | Arg | Val | Glu | His | Val | Asp | His | Ser | Arg | Lys |
| 305 | | | | | 310 | | | | | 315 | | | | | 320 |

| Ser | Ala | Glu | Gln | Ala | Val | Lys | Ala | Ile | Phe | Ala | Ser | Glu | Gln | Gly | Lys |
| | | | | 325 | | | | | 330 | | | | | 335 | |

| Ser | Val | Asp | Glu | Tyr | Asp | Tyr | Leu | Pro | Tyr | Phe | Tyr | Ser | Arg | Ala | Phe |
| | | | 340 | | | | | 345 | | | | | 350 | | |

| Asp | Leu | Ser | Trp | Gln | Phe | Tyr | Gly | Asp | Asn | Val | Gly | Glu | Thr | Val | Leu |
| | | 355 | | | | | 360 | | | | | 365 | | | |

| Phe | Gly | Asp | Ala | Asp | Pro | Asn | Ser | Ala | Thr | His | Lys | Phe | Gly | Gln | Tyr |
| | 370 | | | | | 375 | | | | | 380 | | | | |

| Trp | Ile | Lys | Asp | Gly | Lys | Ile | Val | Gly | Ala | Phe | Leu | Glu | Ser | Gly | Ser |
| 385 | | | | | 390 | | | | | 395 | | | | | 400 |

Pro Glu Glu Asn Lys Ala Ile Ala Lys Val Ala Lys Val Gln Pro Pro
                405                 410                 415

Ala Thr Leu Asp Gln Leu Ala Gln Glu Gly Ile Ser Phe Ala Ser Lys
                420             425                 430

Ile ( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: modified_base
        ( B ) LOCATION: 3
        ( C ) IDENTIFICATION METHOD: experimental
        ( D ) OTHER INFORMATION: /evidence=EXPERIMENTAL
            / mod_base= i
            / note= "N=i"

( i x ) FEATURE:
        ( A ) NAME/KEY: modified_base
        ( B ) LOCATION: 9
        ( C ) IDENTIFICATION METHOD: experimental
        ( D ) OTHER INFORMATION: /evidence=EXPERIMENTAL
            / mod_base= i
            / note= "N=i"

( x i ) SEQUENCE DESCRIPTION: SEQ ID NO:3:

CCNGARCCNT GGTGYATGCC          20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:4:

TTDATNCCNC CYTTYTCYTC          20

NUCLEIC ACIDS ENCODING ASCORBATE FREE RADIAL REDUCTASE AND THEIR USES

BACKGROUND OF THE INVENTION

This invention relates to plant molecular biology. In particular, to nucleic acid sequences and methods for modifying ascorbic acid levels in transgenic plants.

Ascorbic acid plays essential roles in the metabolism of both plant and animal cells. Among other functions, ascorbic acid serves as a general reducing agent and scavenger of free radicals (Sauberlich, *Annu. Rev. Nutr.* 14:371–391 (1994)). Activated oxygen species (e.g., $O_2^-$ and $H_2 O_2$) resulting from metabolism can, if unquenched, propagate a chain reaction of free radical production, leading to extensive degradation of membrane lipids, proteins, nucleic acids and chlorophyll (Thompson et al., *New Phytol.* 105:317–344 (1987)).

The role of ascorbic acid as a scavenger of free radicals has been shown to be important to protecting plants from a number of environmental stresses. For example, it has been implicated in plant detoxification of ozone (Tanaka et al., *Plant Cell Physiol* 26:1425–1431 (1985); Luwe et al., *Plant Physiol.* 101:969–967( 1993)) and of respiratory-produced $H_2O_2$ during wheat seed germination (Cakmak et al. *J. Exp Bot.* 44:127–132 (1993)). In addition, increases in the levels of ascorbic acid have been noted in response to a variety of plant stresses, including chilling injury (Kuroda et al., *Plant Cell Physiol.* 32:635–641 (1991)), strong illumination in wheat leaves (Mishra et al., *Plant Physiol.* 102:903–910 (1993)), $SO_2$ and $O_3$ in conifer needles (Mehlhorn et al., *Plant Physiol.* 82:336–338 (1986)), cold acclimation in spinach leaves (Schoner and Krause, *Planta* 180:383–389 (1990)), drought in grasses (Smirnoff and Colombe, *J. Exp. Bot.* 1097–1108 (1988)), and increases in oxygen tension in soybean nodules (Dalton et al., *Plant Physiol* 812–818 (1991)) and submerged rice seedlings (Ushimura et al., *Plant Cell Physiol.* 33:1065–1071 (1992)). Furthermore, a correlation between high ascorbic acid content, and nematode resistance in tomato plants has been reported (Arrigoni et al., *Phytopathol* 69:579–581 (1979); Arrigoni et al., *FEBS Lett.* 125: 242–244 (1981)).

As a consequence of scavenging free radicals, ascorbate produces its own free radical, ascorbate free radical (AFR, also called monodehydroascorbate). AFR resulting from the oxidation of ascorbic acid can spontaneously disproportionate to ascorbic acid and dehydroascorbate (Bielski et al., *J. Am. Chem. Soc.* 103:3516–3518 1981), the latter being converted back to ascorbic acid by dehydroascorbate reductase using glutathione as electron donor (Law et al., *Biochem. J.* 210:899–903 (1983)). However, most AFR is directly reduced to ascorbic acid by the action of AFR reductase (monodehydroascorbate reductase, NADH:AFR oxidoreductase, EC 1.6.5.4), using NADH or NADPH as electron donor (Hossain and Asada, *J. Biol. Chem.* 260:12920–12926 (1985)). By these mechanisms, ascorbate is maintained in its reduced form as a protectant against cellular oxidative degradation.

High levels of AFR reductase activity, are found in chloroplasts (Hossain et al., *Plant Cell Physiol* 25:385–395 (1984)). Activity is also found in mitochondria, the cytosol and in microsome preparations, (Arrigoni et al., *FEBS Lett.* 125: 242–244 (1981); Yamauchi et al., *J. Japan Soc Hort Sci* 53:347–353 (1984)), on glyoxsomal membranes (Bowditch and Donaldson *Plant Physiol* 94:531–537 (1990)) and in the cell wall (Dalton et al., *Plant Physiol* 102:481–489 (1993)). AFR reductase thus appears to be widely distributed among plant species and tissues.

The AFR reductase enzyme is a monomer and contains 1 mol of FAD per mol of enzyme (Hossain and Asada, *J. Biol Chem* 260:12920–12926 (1985)). When purified to homogeneity it has a molecular mass of 47 kD from cucumber fruit (Hossain and Asada, 1985), 42 kD from potato tuber (Borraccino et al., Planta 167:521–526 (1986)) and is present as isozymes of 39 and 40 kD in soybean root nodules (Dalton et al., *Arch. Biochem. Biophys.* 292:281–286 (1992) ). AFR reductase has been cloned from cucumber fruit (Sano and Asada, *Plant Cell Physiol.* 35:425–437 (1994)) and pea (Murthy and Zilinskas, *J. Biol. Chem.* 269:31129–31133 (1994)), but so far no information is available on the expression of the gene.

Many traits in plants can be modified by manipulation of ascorbate free radical reductase levels and thus ascorbic acid levels in important crop plants. Thus, the isolation and characterization of nucleic acids encoding AFR reductase from plant species would be useful in developing new cultivars with improved characteristics. The present invention addresses these and other needs.

SUMMARY OF THE INVENTION

The present invention provides isolated nucleic acid constructs comprising tomato AFR reductase polynucleotide sequences. The polynucleotides encode AFR reductase polypeptides having ability to catalyze the reduction of AFR. The polypeptides typically have a motif involved in the binding of FAD or NAD(P)H to the polypeptide, such as the polypeptide as shown in SEQ ID No.: 2. The polynucleotide sequence can be either full length or a fragment of the full length gene. An exemplary AFR reductase polynucleotide is shown in SEQ ID No.: 1.

The nucleic acid constructs of the invention may also comprise an expression cassette for transcription and translation of the AFR reductase polynucleotide. In these embodiments, the construct further comprises a promoter operably linked to the AFR reductase polynucleotide sequence. The promoter may be either inducible or constitutive. The invention further provides transgenic plants comprising the recombinant expression cassettes. The transgenic plant may be any plant, for instance, tomato.

Also claimed are methods of enhancing resistance to oxidative stress in a plant. The methods comprise introducing into plant tissue a recombinant expression cassette comprising a plant promoter operably linked to a tomato AFR reductase polynucleotide sequence. Regenerating the plant tissue into a whole plant, whereby the regenerated plant expresses an AFR reductase polynucleotide, and selecting plants having enhanced resistance to oxidative stress. The recombinant expression cassette can be introduced into the plant by a variety of methods, for instance, using Agrobacterium.

DEFINITIONS

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants. It includes plants of a variety of ploidy levels, including polyploid, diploid and haploid.

A "heterologous sequence" is one that originates from a foreign species, or, if from the same species, is substantially modified from its original form. For example, a heterologous promoter operably linked to structural gene is from a species different from that from which the structural gene was derived, or, if from the same species, is substantially modified from its original form.

An "AFR reductase polynucleotide sequence" is a subsequence or full length polynucleotide sequence of an AFR reductase gene, such as the tomato AFR reductase gene, which, when present in a transgenic plant has the desired effect, for example, increasing ascorbic acid levels in the plant. An exemplary polynucleotide of the invention is the coding region of SEQ ID. No: 1. An AFR reductase polynucleotide is typically at least about 1000 nucleotides to about 1700 nucleotides in length, usually from about 1200 to about 1500.

An "AFR reductase polypeptide" is a gene product of an AFR reductase polynucleotide sequence, which has the enzymatic activity of AFR reductase, i.e., the ability to catalyze the reduction of AFR to ascorbic acid. An exemplary polypeptide of the invention is SEQ ID No.: 2.

The phrases "biologically pure" or "isolated" refer to material which is substantially or essentially free from components which normally accompany it as found in its native state. Typically, a protein or nucleic acid is substantially pure when at least about 95% of the protein or nucleic acid in a sample has the same amino acid or nucleotide sequence. Usually, protein that has been isolated to a homogenous or dominant band on a polyacrylamide gel, trace contaminants in the range of 5–10% of native protein which co-purify with the desired protein. Biologically pure material does not contain such endogenous co-purified protein.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional AFR reductase polypeptide, one of skill will recognize that because of codon degeneracy, a number of polynucleotide sequences will encode the same polypeptide. These variants are specifically covered by the above term. In addition, the term "polynucleotide sequence from an AFR reductase gene" specifically includes those full length sequences substantially identical (determined as described below) with an AFR reductase gene sequence and that encode proteins that retain the function of the AFR reductase protein. Thus, in the case of tomato AFR reductase gene disclosed here, the above term includes variant polynucleotide sequences which have substantial identity with the sequences disclosed here and which encode proteins capable of modulating ascorbate levels in plant tissues as detected in using standard assays.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a segement or "comparison window" to identify and compare local regions of sequence similarity. The segment used for purposes of comparison may be at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%.

Another indication that nucleotide sequences are substantially identical is if two molecules hybridize to each other under stringent conditions. Stringent conditions are sequence dependent and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code.

As used herein, a homolog of a particular AFR reductase gene (e.g. the tomato AFR reductase gene) is a second gene (either in the same plant type or in a different plant type)

which has a polynucleotide sequence of at least 50 contiguous nucleotides which are substantially identical (determined as described above) to a sequence in the first gene. It is believed that, in general, homologs share a common evolutionary past.

DESCRIPTION OF THE PREFERRED EMBODIMENT

Figure 1A:
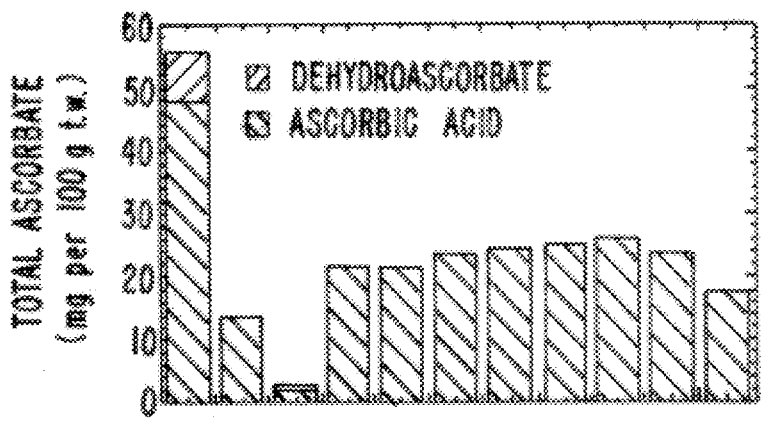
FIGS. 1A-C show total ascorbate, AFR reductase activity and mRNA abundance in tomato tissues. (A) Total ascorbate levels. Ascorbic acid was determined using an ion exclusion column with detection at 245 nm. Dehydroascorbate was determined after reduction to ascorbic acid. (B) AFR reductase activity, measured by following the oxidation of NADH at 340 nm due to AFR generated with ascorbate oxidase. (C) AFR reductase, RNA abundance, estimated against a standard curve using ribonuclease protection assays. (Fruit IG, immature green; MG mature green; BR, breaker; TU, turning; PK, pink; LR. light red; RR, red ripe; OR, over ripe).
Figure 1B:
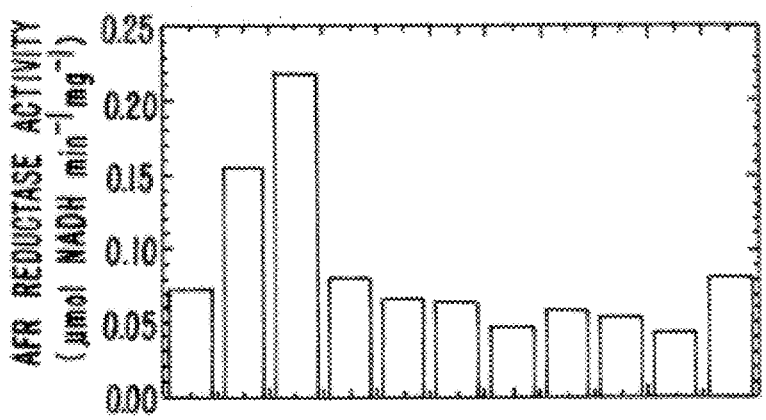

This invention relates to plant genes encoding AFR reductase. Nucleic acid sequences from AFR reductase genes can be used to manipulate AFR reductase levels and thereby control ascorbic acid level in plants. Modulation of ascorbic acid levels can be used to provide improved resistance to oxidative stresses, including chilling and heat injury, drought and wilting stress, oxidizing atmospheric pollutants (ozone, oxides of nitrogen, and oxides of sulfur), and scorching injury due to excess light. In addition, plant resistance to infection by nematodes and other plant pests and pathogens can be enhanced. Other uses of AFR reductase nucleic acid sequences include increasing the ascorbic acid (vitamin C) content of edible plant tissues (e.g., fruit), increasing the nitrogen fixing ability of plants such as legumes, and to improve the photosynthetic capacities of plant organs.

The invention has use in altering ascorbate acid levels in all higher plants. The invention thus has use over a broad range of types of plants, including species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Lolium, Zea, Triticum, Sorghum, and Datura.

The Example section below, which describes the isolation and characterization of the AFR reductase gene in tomato, is exemplary of a general approach for isolating AFR reductase genes. The isolated genes can then be used to construct recombinant vectors for altering AFR reductase gene expression in transgenic plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of AFR reductase genes may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as fruit, and a cDNA library which contains the AFR reductase gene transcript is prepared from the mRNA. Alternatively, cDNA may be prepared from mRNA extracted from other tissue types (organs) in which AFR reductase genes or homologs are expressed such as seeds, leaves, stems, and roots.

The cDNA or genomic library can then be screened using a probe based upon the sequence of a cloned AFR reductase gene such as tomato AFR reductase disclosed here. Probes may be used to hybridize with genomic DNA or cDNA sequences to isolate homologous genes in the same or different plant species.

Alternatively, polynucleotides may be synthesized by well-known techniques as described in the technical literature. See, e.g., Carruthers et al., *Cold Spring Harbor Symp. Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Transposon tagging can also be used for isolation of the relevant gene. Transposon tagging involves introducing a transposon into the plant which leads to a mutation of the target gene and a detectable phenotypic change in the plant. Using a probe for the transposon, the mutant gene can then be isolated. Using the DNA adjacent to the transposon in the isolated mutant gene as a probe, the normal wild type allele of the target gene can be isolated. See, e.g., Haring, et al., *Plant Mol. Biol.* 16:449-469 (1991) and Walbot, *Ann. Rev. Plant Mol. Biol.* 43:49-82 (1992).

Isolated sequences prepared as described herein can then be used to enhance or increase endogenous AFR reductase gene expression and therefore increase ascorbic acid levels in desired plant tissues. Where overexpression of the AFR reductase gene is desired, an AFR reductase gene from a different species may be used to decrease potential sense suppression effects. For instance, the tomato AFR reductase gene can be used to increase expression in pea, cucumber, soybean, peppers, strawberry, squash, wheat, rice or corn.

One of skill will recognize that the nucleic acid encoding a functional AFR reductase enzyme (e.g., SEQ ID No.: 2) need not have a sequence identical to the exemplified gene disclosed here. In addition, the polypeptides encoded by the AFR reductase genes, like other proteins, have different domains which perform different functions. Thus, the AFR reductase gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

The isolated sequences prepared as described herein, can also be used in a number of techniques to suppress endogenous AFR reductase gene expression. For instance, antisense or sense suppression, as well as ribozymes can be conveniently used to inhibit AFR reductase gene expression. Because dehydroascorbate is a cofactor in some biochemical reactions, such as ethylene formation, reduction in AFR reductase activity is useful in promoting these reactions.

To use isolated AFR reductase sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988).

A DNA sequence coding for the desired AFR reductase polypeptide, for example a cDNA sequence encoding a full length protein, will be used to construct a recombinant expression cassette which can be introduced into the desired plant. An expression cassette will typically comprise the AFR reductase polynucleotide operably linked to transcriptional and translational initiation regulatory sequences which will direct the transcription of the sequence from the AFR reductase gene in the intended tissues of the transformed plant.

For example, a plant promoter fragment may be employed which will direct expression of the AFR reductase in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumafeciens*, and other transcription initiation regions from various plant genes known to those of skill.

Alternatively, the plant promoter may direct expression of the AFR reductase gene in a specific tissue or may be otherwise under more precise environmental or developmental control. Such promoters are referred to here as "inducible" promoters. Examples of environmental conditions that may effect transcription by inducible promoters include anaerobic conditions or the presence of light.

Examples of promoters under developmental control include promoters that initiate transcription only in certain tissues, such as fruit, seeds, or flowers. An exemplary fruit-specific promoter is the promoter from the E8 gene (Deikman & Fischer, *EMBO J.* 7:3315 (1988)). The operation of a promoter may also vary depending on its location in the genome. Thus, an inducible promoter may become fully or partially constitutive in certain locations.

If proper polypeptide expression is desired, a polyadenylation region at the 3'-end of the AFR reductase coding region should be included. The polyadenylation region can be derived from the natural gene, from a variety of other plant genes, or from T-DNA.

The vector comprising the sequences from an AFR reductase gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Such DNA constructs may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *EMBO J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

*Agrobacterium tumefaciens*-meditated transformation techniques are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired AFR reductase-controlled phenotype. Such regeneration techniques rely on manipulation of certain phytohormones in a tissue culture growth medium, typically relying on a biocide and/or herbicide marker which has been introduced together with the AFR reductase nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The methods of the present invention are particularly useful for incorporating the AFR reductase polynucleotides into transformed plants in ways and under circumstances which are not found naturally. In particular, the AFR reductase polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The effect of the modification of AFR reductase gene expression can be measured by detection of increases or decreases in mRNA levels using, for instance, Northern blots. In addition, the phenotypic effects of altering expression can be detected by measuring ascorbic acid levels in the plant. Ascorbic acid levels are measured using conventional assay techniques, such as by HPLC as described below. The transgenic plants of the invention will typically have increased ascorbic acid levels as compared to the parent lines from which they were derived. Typically, using the assays described below, ascorbic acid levels (not including dehydroascorbate) will be at least about 20 mg/100 g fresh weight, usually at least about 30 mg/100 g fresh weight, and preferably more than 50 mg/100 g fresh weight.

The following Example is offered by way of illustration, not limitation.

MATERIALS AND METHODS
Plant Material and Preparation of RNA

Tissue of tomato (*Lycopersicon esculentum* Mill.) cvs. T5 and Castlemart was collected from mature field-grown plants. Fresh fruit at defined ripening stages and vegetative tissues were used immediately for determination of ascorbic acid and dehydroascorbate levels, while identical samples were frozen in liquid $N_2$ and stored at −80° C. for subsequent assays of AFR reductase activity and preparation of RNA.

RNA was prepared from young vegetative tissues by powdering in liquid $N_2$ in a pestle and mortar followed by blending with a Tissumizer homogenizer (Tekmar, Cincinatti, Ohio) using the method of Chomczynski and Sacchi *Anal. Biochem.* 162: 156–159 (1987), except that the guanidine thiocyanate concentration was increased to 5M and RNA was subsequently purified by precipitation in 2M LiCl. RNA was prepared from frozen fruit pericarp tissue by powdering in a coffee grinder in the presence of a chip of dry ice, homogenizing in 1M Tris-HCl, pH 9:phenol:chloroform (2:1:1, by vol.), precipitating in 2M LiCl and removing carbohydrate by two precipitations with 33% (v/v) ethanol. RNA prepared by either method was quantified by measuring absorbance at 260 nm, and was relatively free from contaminating proteins and carbohydrate as shown by the $A_{260}/A_{280}$ (typically >1.7) and $A_{260}/A_{230}$ (typically >2.0) ratios.

RNA from control and wounded leaf, stem, green fruit and pink fruit was a generous gift of Dr. Jürg Oetiker. RNA was prepared from greenhouse-grown fruit pericarp tissue (cv. Caruso) which had either frozen immediately in liquid $N_2$, or sliced into 0.5 cm cubes and incubated on filter paper moistened with 50 mM phosphate buffer, pH 7.0/50 µg ml$^{-1}$ chloramphenicol at 25° C. for 6 h, then frozen in liquid $N_2$ (Lincoln et al., *J. Biol. Chem.* 268:19422–19430 (1993)). Leaf and stem tissue (cv VF36) were obtained from greenhouse-grown plants 80 cm tall, and either frozen immediately in liquid $N_2$ or wounded by slicing into 5 mm squares or 2 to 5 mm pieces, respectively, then incubated as above for 5.5 h before preparation of RNA using the method of Lincoln et al. (1993). Wounded root tissue (cv. Castlemart) was prepared from a plant grown in a pot in the greenhouse, from which the soil was carefully washed away in a stream of water. Half of the roots were frozen immediately in liquid $N_2$, and the other half wounded for 5.5 h as described for stem tissue. RNA was extracted using the guanidine thiocyanate method described above.

PCR Amplification

All nucleic acid techniques were as described in Sambrook et al. (1989) unless otherwise noted. Alignments of the monodehydroascorbate reductase sequence from cucumber (Sano and Asada, (1994)) and a partial cDNA sequence in the rice expressed sequence tag library (GenBank accession number D24305) which was highly homologous to cucumber monodehydroascorbate reductase were used to identify conserved amino acid domains for construction of degenerate PCR primers. The 5' primer (5'-CCiGA(AG)CCiTGGTG(CT)ATGCC-3') SED ID No.:3 corresponded to amino acids 194 to 200 and the 3' primer (5'-TT(AGT)AT(ACGT)CC(ACGT)CC(CT)TT(CT)TC(CT)TC-3') (SEQ. ID. NO: 4) to amino acids 274 to 280 of the tomato sequence, where i=inosine. PCR was carried out in final volumes of 50 µl using 1.0 unit of AmpliTaq (Perkin-Elmer, Norwalk, Conn.)., 200 µM dNTPs and 10 µM primers with 0.5 µg cDNA derived from tomato leaf total RNA as template. Amplifications were for 40 cycles, each consisting of 1 min at 94° C., 1.5 min at 51° C. and 1 min at 72° C. The resulting 261 bp DNA fragment was gel purified and cloned into pCR-Script (Stratagene Inc., La Jolla, Calif.) following the manufacturer's instructions. DNA sequence was determined with universal primers using [$^{35}$S]dATP (NEN, Boston, Mass.) and the Sequenase version 2.0 sequencing kit (United States biochemical Corp., Cleveland Ohio) according to the manufacturer's instructions.

Screening a cDNA Library

Colonies (80,000) of a red ripe tomato fruit cDNA library in the vector pARC7 (DellaPenna et al., *Proc. Natl. Acad. Sci. USA* 83:6420–6424 (1986)) were grown on nitrocellulose filters (Schleicher & Schuell, Keene, N.H.) and replica colony filters subsequently lifted as described in Sambrook et al. (1989). The 261 bp PCR product described above was radioactively labeled by random hexamer priming using [$^{32}$P]dATP (3000 Ci mmol$^{-1}$, NEN) and Klenow DNA polymerase (Pharmacia, Piscataway, N.J.). Probe (approximately 7×10$^8$ dpm µg$^{-1}$) was purified from unincorporated nucleotides by centrifugation through a spin column of Sephadex G-50 (Pharmacia), then used for colony screening. Hybridization was carried out in 50% (v/v) formamide/6×SSPE/5× Denhardt's reagent/0.5% (w/v) SDS/ 100 µg ml$^{-1}$ base-denatured salmon sperm DNA at 38° C., where 1×SSPE=150 mM NaCl/10 mM Na-phosphate/1 mM EDTA, pH 7.4. Filters were washed three times in 6×SSC/ 0.1% SDS at room temperature followed by three high-stringency washes in 0.5×SSC/0.5% SDS at 56° C., where 1×SSC=150 mM NaCl/15 mM Na-citrate, pH 7.0. A secondary screen yielded three cDNAs, of approximately 1.8, 1.7 and 0.85 kb, respectively. Inserts were subcloned from the library vector into pBluescript II SK+plasmid (Stratagene) using the XbaI restriction site. The largest clone was completely sequenced on both strands using universal and a total of 14 specific internal primers synthesized by Genset Corporation (La Jolla, Calif.).

Southern Analysis

Genomic DNA was prepared from young tomato leaves using the method of Chetelat and DeVerna *Theor. App. Genet.* 82:704–712 (1991), and 10 µg samples digested with excess amounts of EcoRI, EcoRV, HindIII or BamHI (New England Biolabs, Beverly, Mass.). Restriction fragments were subjected to electrophoresis through a 0.8% (w/v) agarose gel then transferred to Hybond-N hybridization membrane (Amersham, Arlington Heights, Ill.). The resulting blot was hybridized with radiolabeled probe, prepared as described above for colony screening, in 50% formamide/ 6×SSPE/5×Denhardt's reagent/0.5% SDS/100 µg ml$^{-1}$ base-denatured salmon sperm DNA at 38° C. ($T_m$−27° C.) for 17 h. The blot was washed three times in 6×SSC/0.1% SDS at room temperature followed by three high-stringency washes in 0.5×SSC/0.5% SDS at 56° C. ($T_m$−24° C.), then exposed to pre-flashed X-Omat AR film (Kodak, Rochester, N.Y.) with an intensifying screen at −80° C. for 2d.

Northern Analysis

Tomato stem total RNA (20 µg) was subjected to electrophoresis on a 1.2% agarose/10% (v/v) formaldehyde denaturing gel then transferred to Hybond-N membrane.

The blot was hybridized and washed exactly as for the Southern blot described above, and exposed to film for 6 d.

Determination of Ascorbic Acid and Total Ascorbate

Assays for the reduced and oxidized species of ascorbic acid (ascorbic acid and dehydroascorbate, respectively) were performed using HPLC, essentially as described by Graham and Annette J. Chromatog. 594:187–194 (1992). Fresh vegetative tissue or fruit pericarp (10 g, composed of 3.33 g from each of three representative samples) was homogenized for 3 min in 100 ml 62.5 mM metaphosphoric acid (Aldrich, Milwaukee, Wis.) using a bottom-driven homogenizer. Volume was brought to 150 ml with metaphosphoric acid solution, extracts centrifuged at 6500× g for 15 min at 4° C. then supernatants filtered through Miracloth (Calbiochem, La Jolla, Calif.). Samples for assays were filtered through 0.45 µm cellulose acetate filters (Corning Glass, Corning, N.Y.) prior to use. Ascorbic acid was determined directly from these extracts. Total ascorbate was estimated in 250 µl aliquots reduced by adding 42 µl 30 µM dl-homocysteine (Aldrich), then adjusted to pH 6.8 to 7.0 by slow addition of 125 µl 2.6M $K_2HPO_4$. Reduction was stopped after 30 min by addition of 333 µl 6.25M metaphosphoric acid. Samples (20 µl) were injected onto a 300×7.8 mm Aminex HPX-87H column (Bio-Rad, Hercules, Calif.) attached to a LDC Constametric IIIG pump (Milton Roy, Rochester, N.Y.), operated at room temperature using 4.5 mM $H_2SO_4$ as eluant at a flow rate of 0.5 ml min$^{-1}$. Ascorbic acid was monitored at 245 nm (retention time 11.4 min) with a SPD-6AV spectrophotometric detector (Shimadzu, Columbbia, Md.) attached to a chart recorder and CR601 integrator (Shimadzu). Peaks were converted to concentrations by using dilutions of stock ascorbic acid to construct a standard curve (Graham and Annette, 1992). Dehydroascorbate was calculated by subtraction of ascorbic acid values from total ascorbate.

Assay for Ascorbate Free Radical Reductase Activity

Frozen vegetative tissue or fruit pericarp (3 g, composed of 1 g from each of three representative samples) was powdered in liquid $N_2$ using a pestle and mortar, then homogenized at 0° C. for 4 min in 10 ml 0.2M K-phosphate pH 7.8/1 mM EDTA/5 mM $MgCl_2$/0.1% (w/v) BSA/10 mM 2-mercaptoethanol/0.005% (v/v) Triton X-100 using a Tekmar homogenizer. Extracts were centrifuged at full speed in a bench-top centrifuge for 30 min at 0° C., supernatants filtered through Miracloth and 15 µl aliquots assayed in a final reaction volume of 1 ml. AFR reductase activity was determined spectrophotometrically by following the decrease in absorbance at 340 nm due to NADH oxidation caused by AFR generated with ascorbate oxidase (Hossain et al., Plant Cell Physiol. 25:385–395 (1984)).

Protein was estimated using a protein assay dye reagent kit (Bio-Rad) with BSA as standard.

Ribonuclease Protection Assays

Radiolabeled RNA probe (approximately 8×10$^8$ dpm µg$^{-1}$) was prepared by in vitro transcription using as template the 261 bp PCR product subcloned into pCR-Scrip described above, which had previously been linearized with NotI and gel purified. Reactions were performed in the presence of 0.5 mM ATP, CTP and GTP, 5.25 µM UTP, 50 µCi [α-$^{32}$P]UTP (3000 Ci mmol-$^{1}$, NEN) and T7 RNA polymerase (Epicentre, Madison Wis.). In addition, a tritiated sense transcript (approximately 1×10$^7$ dpm µg$^{-1}$) was prepared from the linearized full-length clone in pBluescript II, using [5-6-$^3$H]UTP (12.7 Ci.mmol-1, NEN) and the appropriate RNA polymerase, for use in construction of a standard curve. Aliquots of total RNA preparations (5 µg) or of tritiated sense transcript were hybridized with the antisense radiolabeled riboprobe. Ribonuclease protection assays were performed using the RPA II kit (Ambion, Austin, Tex.) according to the manufacturer's instructions, except that gels were fixed in 10% acetic acid/ 15% ethanol for 1 h and dried onto paper, before exposing to pre-flashed X-Omat AR film with an intensifying screen at –80° C. for 1 to 4 d. Radioactivity in digested samples was estimated by exposing the dried gels to phosphorimager plates which were scanned with a Fujix BAS 1000 phosphorimager (Fuji Medical Systems, Stamford, Conn.). Analysis of resulting scans was performed using Fujix MacBAS software (Fuji), and relative radioactivities converted to percentage mRNA using the standard curve and assuming that mRNA was 3% of total RNA.

RESULTS

The longest AFR reductase cDNA clone resulting from the library screen consisted of 1709 bp plus a poly (A) tail (SEQ ID No.: 1). An A+T-rich region preceded an open reading frame starting with Met at base 49 and ending with a stop codon at base 1485. The nucleotides surrounding the ATG were conserved in nine out of 12 bases with the consensus sequence for plant translation initiation sites. The open reading frame consisted of 1299 bp, and was interrupted by an intron of 138 bp located after base 643 (base 595 numbering from the ATG translation start site). The intron, which disrupted a Met codon, possessed consensus splice junctions of GT at the 5' end and AG at the 3' end. Presumably, this cDNA was derived from a partially processed mRNA, and this was confirmed by sequencing the equivalent region of the second-longest clone resulting from the library screen, which lacked this intron. An+T-rich 3'-flanking region of 225 bp separated the final amino acid from the beginning of the poly (A) tail. A putative polyadenylation signal was located 27 bp upstream from the polyadenylation start site.

The open reading frame predicted a protein of 433 amino acids. The protein possessed a predicted molecular mass of 47 kD. The predicted protein did not appear to possess eukaryotic targeting sequences, suggesting a cytosolic cellular localization.

Two consensus sequences (fingerprints) involved in the binding of the ADP moiety of FAD or NAD(P)H were detected and are identified in SEQ ID. No.: 1. Each fingerprint consists of a conserved 18-amino acid domain (at residues 7–24 and residues 165–182) separated by a loop in the protein from another conserved 5-amino acid domain (at residues 36–40 and residues 191–196). It is thought that the fingerprint at the N terminus of the protein is involved in the binding of FAD, while the second site, located in the middle of the protein, is involved in the binding of NADH or NADPH (Eggink et al., J. Mol. Biol. 212:135–142 (1990)). In addition, a conserved 11-amino acid domain involved in the binding of the flavin moiety of FAD was present, beginning at residue 287.

Southern analysis of genomic DNA which had been digested with EcoRI, EcoRV, HindIII or BamHI exhibited only a single band when probed at low stringency with the 261 bp PCR product of AFR reductase. This indicates the presence of a single genomic copy of this AFR reductase gene in tomato.

A northern blot of tomato stem total RNA probed with the 261 bp PCR product of AFR reductase showed a single band, of approximately 1.7 kb. The AFR reductase cDNA clone was 1570 bp without the intron, suggesting the addition of about 150 bases of poly (A) to the AFR reductase mRNA.

Total ascorbate (ascorbic acid plus dehydroascorbate) levels were very high in leaf tissue (>50 mg per 100 g fresh weight), lower in stem tissue and very low in roots (FIG. 1A). Root tissue contained only about 3 mg ascorbate per 100 g fresh weight, and a large proportion of this (about 40%) was in the oxidized dehydroascorbate form. In leaves and stems the proportion of total ascorbate present as dehydroascorbate was much lower, about 15% and 2%, respectively. Fruit pericarp tissue contained a relatively constant amount of total ascorbate throughout fruit development and ripening. These levels, of around 20 mg per 100 g fresh weight, increased slightly from early development stages to peak at around the light red stage before declining as fruit became over-ripe. Fruit tissue possessed ascorbate entirely as ascorbic acid, with dehydroascorbate present below the level of detection.

Figure 1C:
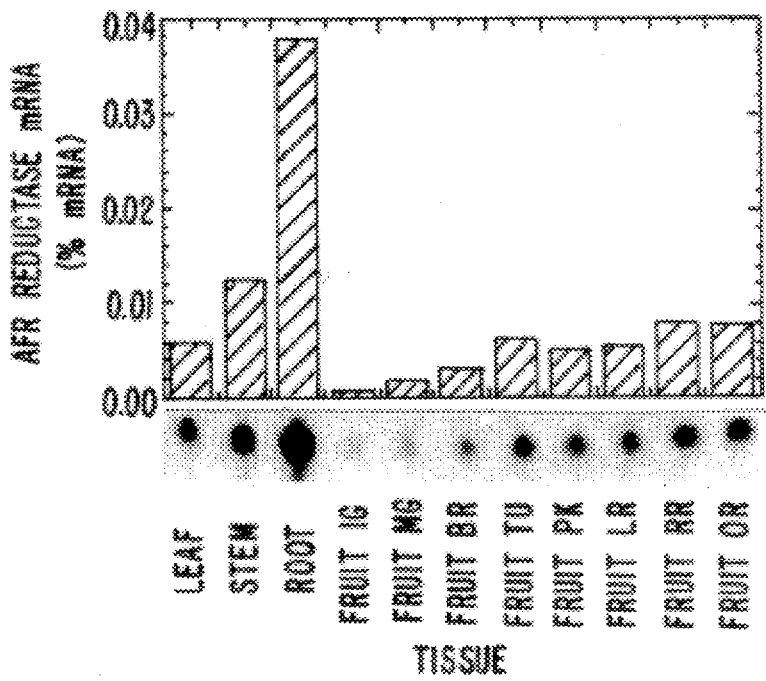

AFR reductase activity showed an inverse correlation with the levels of total ascorbate (FIG. 1A, B). AFR reductase activity was low in leaves where total ascorbate levels were high, and high in stems and roots where total ascorbate levels are low. In fruit AFR reductase activity was higher in early developmental stages, declined as fruits ripened and ascorbate levels increased, and then increased at the over-ripe stage when ascorbate levels declined. AFR reductase mRNA abundance (FIG. 1C) correlated well with AFR reductase activity in vegetative tissue and during fruit ripening. However, during the early stages of fruit growth, relatively low levels of AFR reductase mRNA were detected, yet moderate enzyme activity was evident.

Figure 2:
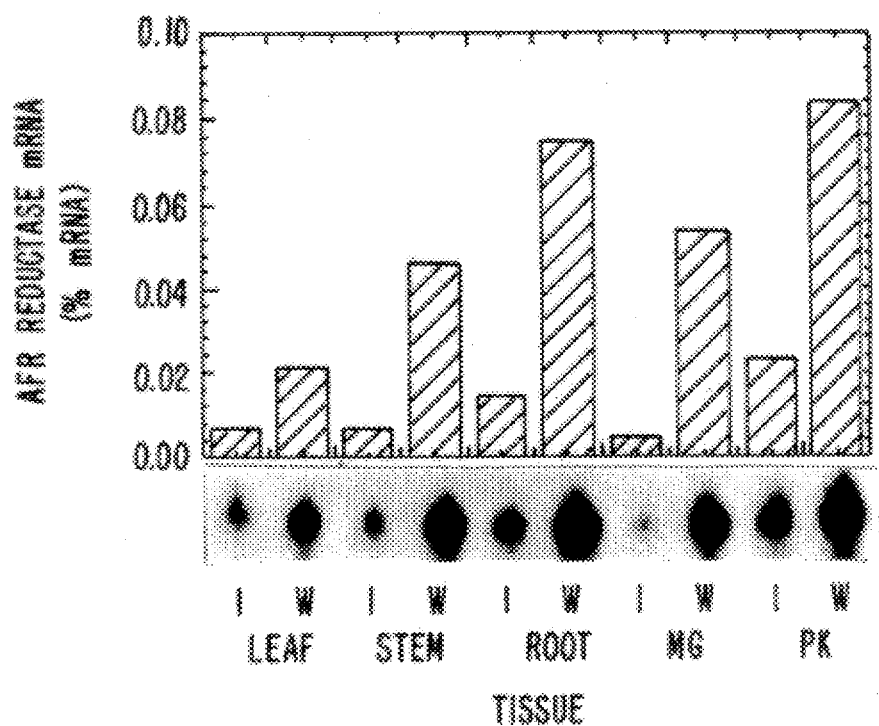
FIG. 2 shows effect of wounding on AFR reductase mRNA abundance. Tissues were either intact (I), wounded (W) by slicing with a razor blade and incubating for 5.5 h (vegetative tissues) or 6 h (fruit). Total RNA was hybridized with a $^{32}$P-labeled AFR reductase probe for assay by ribonuclease protection. (MG, mature green fruit; PK, pink fruit).

Wounding of both vegetative and fruit tissues for 5.5 to 6 h resulted in substantially increased levels of AFR reductase mRNA (FIG. 2). Increases of between 3-and 8-fold relative to unwounded controls were detected, except in mature green fruit where a 15-fold increase was observed. After wounding, levels of AFR reductase mRNA approached 0.1% of mRNA in roots and in pink fruit.

DISCUSSION

Low-stringency Southern analysis suggested the existence of a single genomic gene for AFR reductase in tomato. Two isozymes of AFR reductase have been detected in soybean root nodules (Dalton et al., *Arch. Biochem. Biophys.* 292:281–286 (1992)), and in cucumber a comparison of the sequences of proteolytic fragments of AFR reductase purified from fruit with a cDNA clone derived from seedlings indicated the presence of more than one isozyme (Sano and Asada, 1994). AFR reductase is found in the chloroplast stroma in soluble form but also has been detected in the cytosol, in mitochondria and on microsomal membrane preparations on glyoxsomal membranes and in the cell. The existence of multiple isoforms of AFR reductase, and in multiple cellular locations, suggests that there may be additional genes encoding AFR reductase isoforms in tomato.

AFR reductase enzyme activity levels were inversely correlated with levels of total ascorbate, with the highest enzyme activity and lowest ascorbate levels being observed in roots. It is possible that enzyme levels are regulated by ascorbate demand, such that AFR reductase levels increase in tissues with high rates of ascorbate utilization. This may be particularly important when available pools of total ascorbate are low, as in roots. In addition, there was a close correlation between AFR reductase enzyme activity and AFR reductase mRNA levels. Although the correlation was not perfect, it suggests that AFR reductase enzyme levels are regulated, at least in part, at the level of mRNA abundance.

The possibility that AFR reductase levels are regulated by ascorbate demand was tested by subjecting tomato tissues to mechanical wounding. This treatment causes the increased synthesis of hydroxyproline-rich cell wall glycoproteins, which are formed by the post-translational hydroxylation of peptidyl proline by prolyl hydroxylase in a reaction utilizing ascorbic acid as a reducing agent (De Gara et al., *Phytochemistry* 30:1397–1399 (1991)). Wounding may thus lead to an increased demand for ascorbic acid. In all tissues examined, mechanical wounding triggered a dramatic accumulation of AFR reductase mRNA (FIG. 2).

In addition to increasing ascorbate demand for proline hydroxylation, it is thought that wounding results in the initiation of lipid peroxidation by lipoxygenase, inducing a self-perpetuating wave of free radicals which cause rapid membrane deterioration (Thompson et al., *New Phytol.* 105:317–344 (1987)). Increased synthesis of ascorbate and induction of AFR reductase may occur in adjacent non-wounded cells in order to prevent the spread of damaging free radicals and to localize necrosis to wound or infection sites.

As noted above, ascorbic acid levels have been correlated with resistance to a number of plant stresses including chilling and heat injury, drought and wilting stress, oxidizing atmospheric pollutants (ozone, oxides of nitrogen, and oxides of sulfur), scorching injury due to excess light and various plant pathogens. Thus, the polynucleotides of the invention are useful in improve resistance to these factors as well as in increasing the ascorbic acid for other reasons such as increasing nutritional content of plants.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

---

What is claimed is:

1. An isolated nucleic acid construct comprising a tomato AFR reductase polynucleotide sequence, which polynucleotide hybridizes to SEQ ID No.:1 under stringent conditions.

2. The nucleic acid construct of claim 1, wherein the AFR reductase polynucleotide sequence encodes an AFR reductase polypeptide as shown in SEQ ID No.:2.

3. The nucleic acid construct of claim 1, wherein the polynucleotide sequence is a full length AFR reductase gene.

4. The nucleic acid construct of claim 1, wherein the AFR reductase polynucleotide is as shown in SEQ ID No.:1.

5. The nucleic acid construct of claim 1, further comprising a promoter operably linked to the AFR reductase polynucleotide sequence.

6. The nucleic acid construct of claim 5, wherein the promoter is a tissue-specific promoter.

7. The nucleic acid construct of claim 5, wherein the promoter is a constitutive promoter.

8. A transgenic plant comprising a recombinant expression cassette comprising a plant promoter operably linked to a tomato AFR reductase polynucleotide sequence.

9. The transgenic plant of claim 8, wherein the plant promoter is a heterologous promoter.

10. The transgenic plant of claim 8, wherein the plant is tomato.

11. The transgenic plant of claim 8, wherein the AFR reductase polynucleotide encodes a protein having a motif involved in the binding of FAD or NAD(P)H to the protein.

12. The transgenic plant of claim 8, wherein the AFR reductase polynucleotide sequence encodes an AFR reductase polypeptide as shown in SEQ ID No.:2.

13. The transgenic plant of claim 8, wherein the polynucleotide sequence is as shown in SEQ ID No.1.

14. An isolated AFR reductase polynucleotide sequence which hybridizes to SEQ. ID. No. 1 under stringent condition.

15. The isolated polynucleotide which is as shown in SEQ. ID. No. 1.

16. An isolated polynucleotide which encodes a polypeptide as shown in SEQ. ID. No. 2.

17. A method of increasing AFR reductase gene expression in a plant, the method comprising introducing into the plant a recombinant expression cassette comprising a plant promoter operably linked to an AFR reductase polynucleotide sequence of claim 14.

18. The method of claim 17, wherein the plant is a tomato plant.

19. The method of claim 17, wherein the recombinant expression cassette is introduced into the plant using Agrobacterium.

20. The method of claim 17, wherein the polynucleotide encodes an AFR reductase polypeptide as shown in SEQ. ID. No. 2.

21. The method of claim 17, wherein the polynucleotide sequence is as shown in SEQ. ID. No. 1.

* * * * *